United States Patent
Sugita

(10) Patent No.: US 10,709,344 B2
(45) Date of Patent: Jul. 14, 2020

(54) MEASUREMENT APPARATUS

(71) Applicant: KYOCERA Corporation, Kyoto (JP)

(72) Inventor: Shotaro Sugita, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 814 days.

(21) Appl. No.: 15/313,001

(22) PCT Filed: May 26, 2015

(86) PCT No.: PCT/JP2015/002664
§ 371 (c)(1),
(2) Date: Nov. 21, 2016

(87) PCT Pub. No.: WO2015/182129
PCT Pub. Date: Dec. 3, 2015

(65) Prior Publication Data
US 2017/0188852 A1    Jul. 6, 2017

(30) Foreign Application Priority Data

May 27, 2014  (JP) ................................. 2014-109372

(51) Int. Cl.
*A61B 5/02*  (2006.01)
*A61B 5/026*  (2006.01)
(Continued)

(52) U.S. Cl.
CPC ............ *A61B 5/0261* (2013.01); *A61B 5/026* (2013.01); *A61B 5/0285* (2013.01);
(Continued)

(58) Field of Classification Search
CPC ... A61B 5/0261; A61B 5/6823; A61B 5/6824; A61B 5/6826; A61B 5/6831;
(Continued)

(56) References Cited

U.S. PATENT DOCUMENTS

2012/0302889 A1* 11/2012 Rajan ................... A61B 5/0261
600/455

FOREIGN PATENT DOCUMENTS

JP   63-183042 A   7/1988
JP   3-21208 Y2   5/1991
(Continued)

OTHER PUBLICATIONS

An Office Action issued by the Japanese Patent Office dated Oct. 3, 2017, which corresponds to Japanese Patent Application No. 2014-109372 and is related to U.S. Appl. No. 15/313,001; with English language Concise Explanation.
(Continued)

*Primary Examiner* — Elmer M Chao
(74) *Attorney, Agent, or Firm* — Studebaker & Brackett PC

(57) ABSTRACT

A measurement apparatus includes a housing, a display disposed on the front face of the housing, a contact interface, to be contacted by a test site, disposed on a different surface than the front face of the housing, a laser light source that emits laser light from the contact interface, a light receiver that receives scattered laser light from the test site, a biological information generator that generates biological information based on output from the light receiver, and a controller that controls emission of laser light in the laser light source.

6 Claims, 4 Drawing Sheets

(51) Int. Cl.
    *A61B 5/00*         (2006.01)
    *A61B 5/0285*     (2006.01)
    *A61B 5/145*      (2006.01)

(52) U.S. Cl.
    CPC .......... *A61B 5/6843* (2013.01); *A61B 5/6898* (2013.01); *A61B 5/14542* (2013.01); *A61B 2562/0219* (2013.01)

(58) Field of Classification Search
    CPC ................ A61B 5/6833; A61B 5/6828; A61B 2560/0412; A61B 2562/0219; A61N 1/3956
    See application file for complete search history.

(56) References Cited

FOREIGN PATENT DOCUMENTS

| | | |
|---|---|---|
| JP | H08-308942 A | 11/1996 |
| JP | 2005-69771 A | 3/2005 |
| JP | 2005-130969 A | 5/2005 |
| WO | 2011/162000 A1 | 12/2011 |

OTHER PUBLICATIONS

International Search Report issued in PCT/JP2015/002664; dated Jul. 28, 2015.
Written Opinion issued in PCT/JP2015/002664; dated Jul. 28, 2015; with English language Concise Explanation.

\* cited by examiner

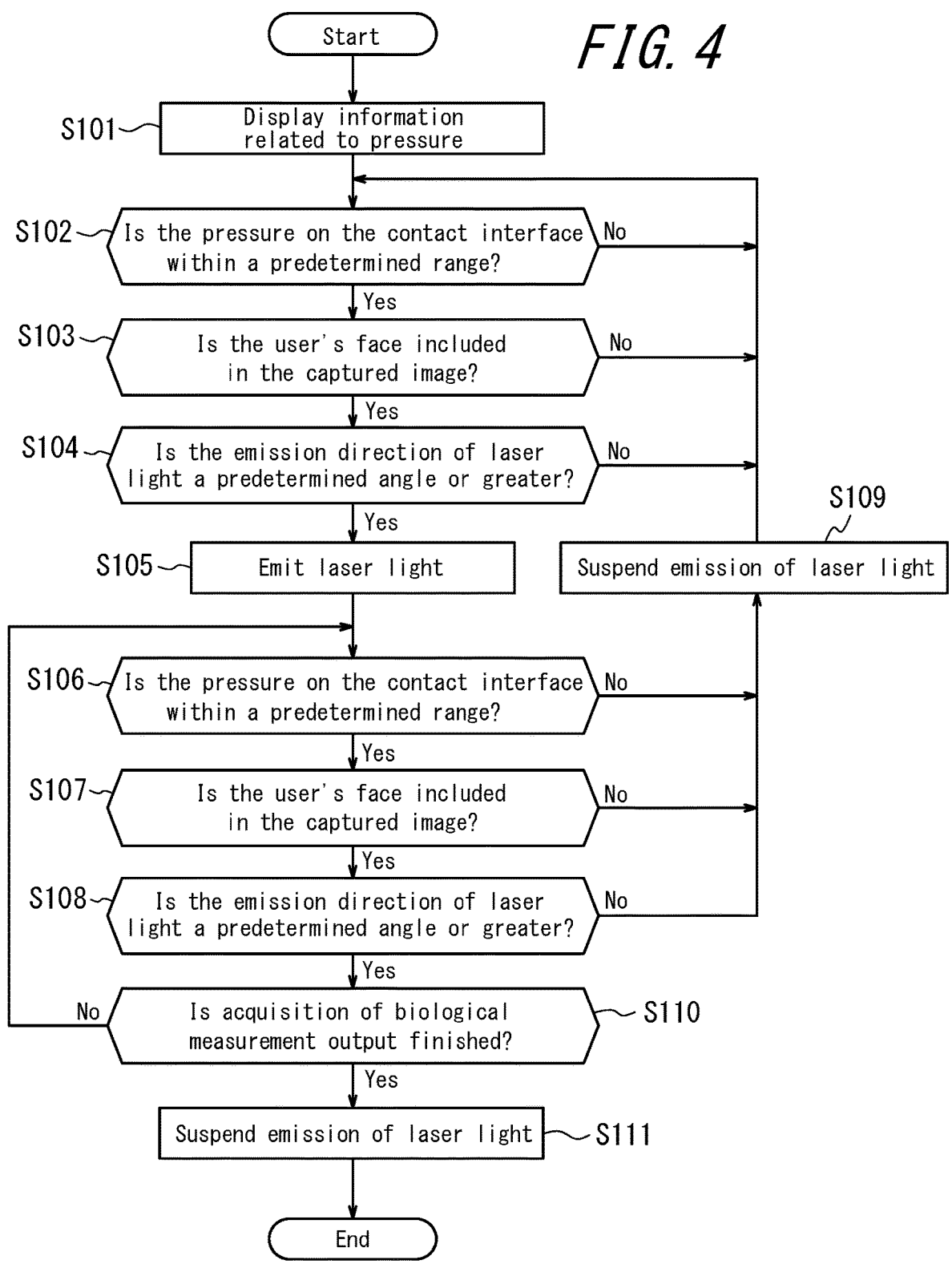

MEASUREMENT APPARATUS

CROSS-REFERENCE TO RELATED APPLICATION

This application claims priority to and the benefit of Japanese Patent Application No. 2014-109372 filed May 27, 2014, the entire contents of which are incorporated herein by reference.

TECHNICAL FIELD

This disclosure relates to a measurement apparatus.

BACKGROUND

An example of an existing measurement apparatus measures biological information by acquiring biological output information from a test site, such as a fingertip of a subject (user).

SUMMARY

A measurement apparatus according to this disclosure includes:

a housing;

a display disposed on a front face of the housing;

a contact interface, to be contacted by a test site, disposed on a different surface than the front face of the housing;

a laser light source configured to emit laser light from the contact interface;

a light receiver configured to receive scattered laser light from the test site;

a biological information generator configured to generate biological information based on output from the light receiver; and a controller configured to control emission of laser light by the laser light source.

BRIEF DESCRIPTION OF THE DRAWINGS

In the accompanying drawings:

FIG. 4 is a flowchart illustrating an example of emission control of laser light by the controller.

DETAILED DESCRIPTION

For example, an existing blood flow measurement apparatus that measures blood flow as the biological information irradiates a fingertip with laser light and measures the blood flow based on scattered light from the blood flow in the capillary at the fingertip. Laser light, however, has high energy due to being highly directional and to the wavelength and phase being aligned. Therefore, in a measurement apparatus that measures biological information by irradiating laser light, the laser light needs to be emitted in an appropriate direction from the perspective of safety.

It would therefore be helpful to provide a safer measurement apparatus.

The following describes one of the disclosed embodiments in detail with reference to the drawings.

Figure 1:
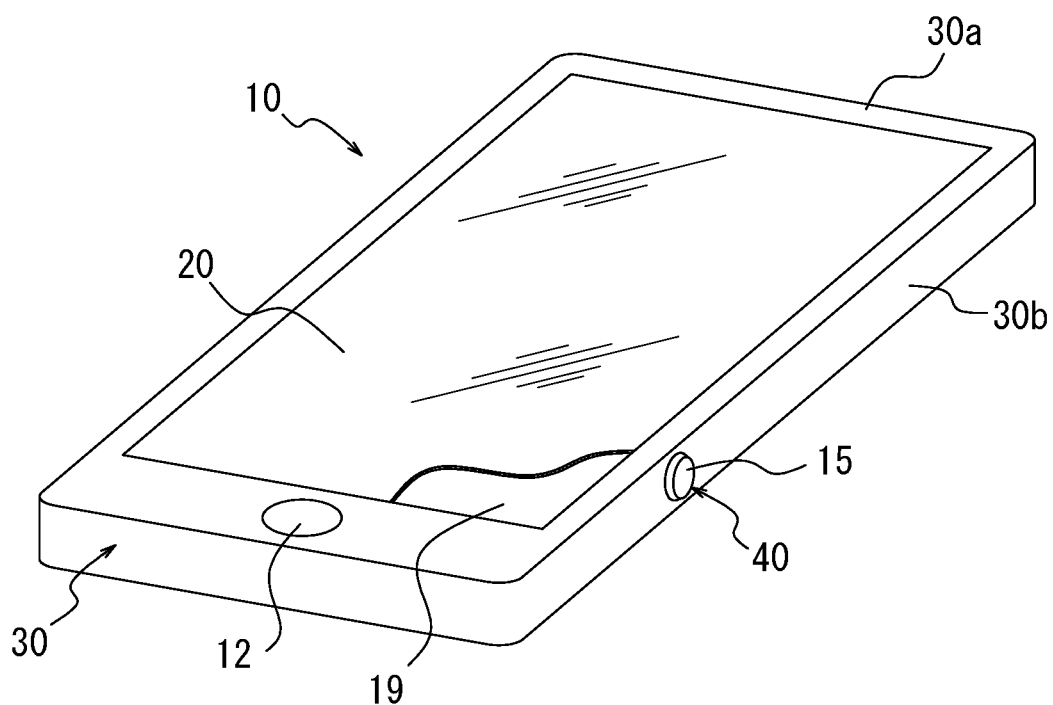
FIG. 1 is an external perspective view schematically illustrating the structure of a measurement apparatus according to one of the embodiments of this disclosure.

FIG. 1 is an external perspective view schematically illustrating the structure of a measurement apparatus according to one of the embodiments of this disclosure. This measurement apparatus 10 may be a measurement apparatus exclusively for measuring a user's biological information, or an electronic device, such as a mobile phone, may be used as the measurement apparatus 10 according to this embodiment. The measurement apparatus 10 is not limited to a mobile phone and may be implemented in any type of electronic device, such as a portable music player, a laptop computer, a wristwatch, a tablet, a game device, or the like.

The measurement apparatus 10 according to this embodiment includes a housing 30 having an approximately rectangular external shape. In the housing 30, a panel 20 is provided at the front face 30a, and as illustrated by the partial cutout of the panel 20 in FIG. 1, a display 19 is held below the panel 20.

The panel 20 is configured using a touch panel that detects contact, a cover panel that protects the display 19, or the like and is, for example, made from glass or a synthetic resin such as acrylic or the like. The panel 20 is, for example, rectangular. The panel 20 may be a flat plate or may be a curved panel, the front face 30a of which is smoothly inclined. When the panel 20 is a touch panel, the panel 20 detects contact by the user's finger, a pen, a stylus pen, or the like. Any detection system may be used in the touch panel, such as a capacitive system, a resistive film system, a surface acoustic wave system (or an ultrasonic wave system), an infrared system, an electromagnetic induction system, a load detection system, or the like. In the present embodiment, for the sake of explanation, the panel 20 is assumed to be a touch panel.

The measurement apparatus 10 according to this embodiment includes a contact interface 15 on a side face 30b, which is one of the long sides of the housing 30. The contact interface 15 is a portion that contacts the test site, such as a finger, in order for the user to measure biological information.

The measurement apparatus 10 according to this embodiment includes a guide 40 that indicates the position of the contact interface 15. The guide 40 for example has a shape, color, and the like that allow recognition of the position of the contact interface 15 when the user looks at the measurement apparatus 10 from the front face 30a. The guide 40 may, for example, be disposed at any position that can specify the position of the contact interface 15 by the user contacting the guide 40 with a finger. As illustrated in FIG. 1, the guide 40 may, for example, be formed as a protrusion that projects from the side face 30b around the contact interface 15. The shape and position of the guide 40 are not, however, limited to this example.

The measurement apparatus 10 includes an imaging unit 12 disposed on the front face 30a. The imaging unit 12 captures an image at the front face 30a of the measurement apparatus 10. The imaging unit 12 may, for example, be configured by a digital video camera.

Figure 2:
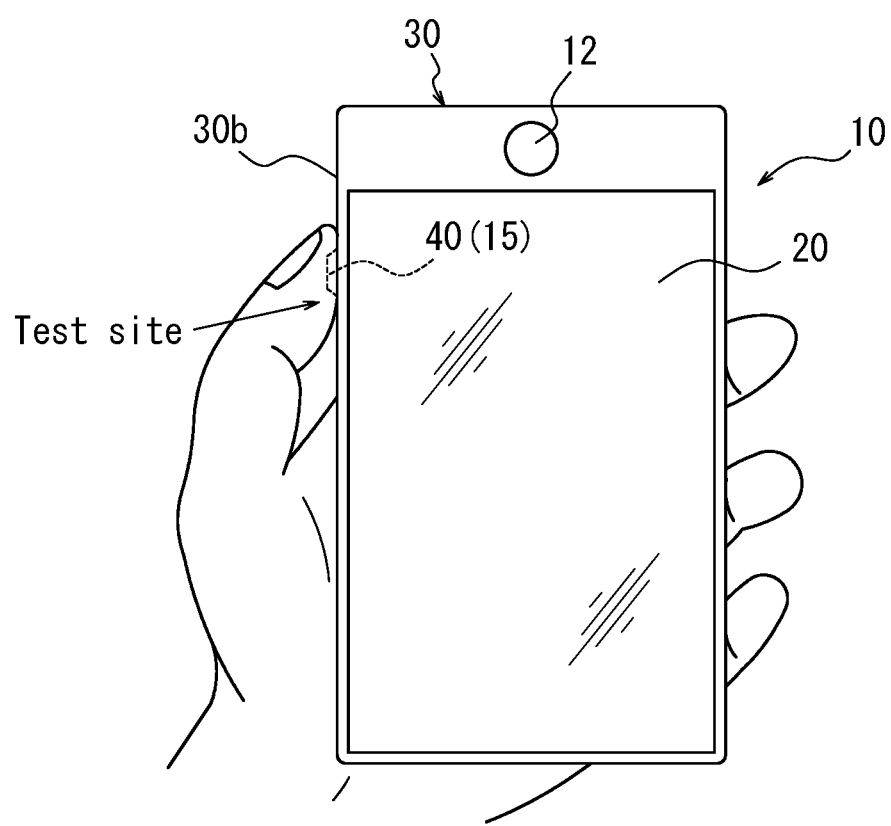
FIG. 2 illustrates the user holding the measurement apparatus of FIG. 1.

The measurement apparatus 10 measures biological information while being held by the user. FIG. 2 illustrates the user holding the measurement apparatus 10 of FIG. 1. As illustrated in FIG. 2, the user for example holds the measurement apparatus 10 in the left hand so that the pad of the left thumb contacts the contact interface 15. The measurement apparatus 10 measures biological information while a finger is being pressed against the contact interface 15, as in FIG. 2. The biological information may be any biological information that can be measured using a biological sensor provided in the measurement apparatus 10. In this embodiment, as one example, the measurement apparatus 10 is described as measuring the user's amount of blood flow, which is information related to blood flow.

Figure 3:
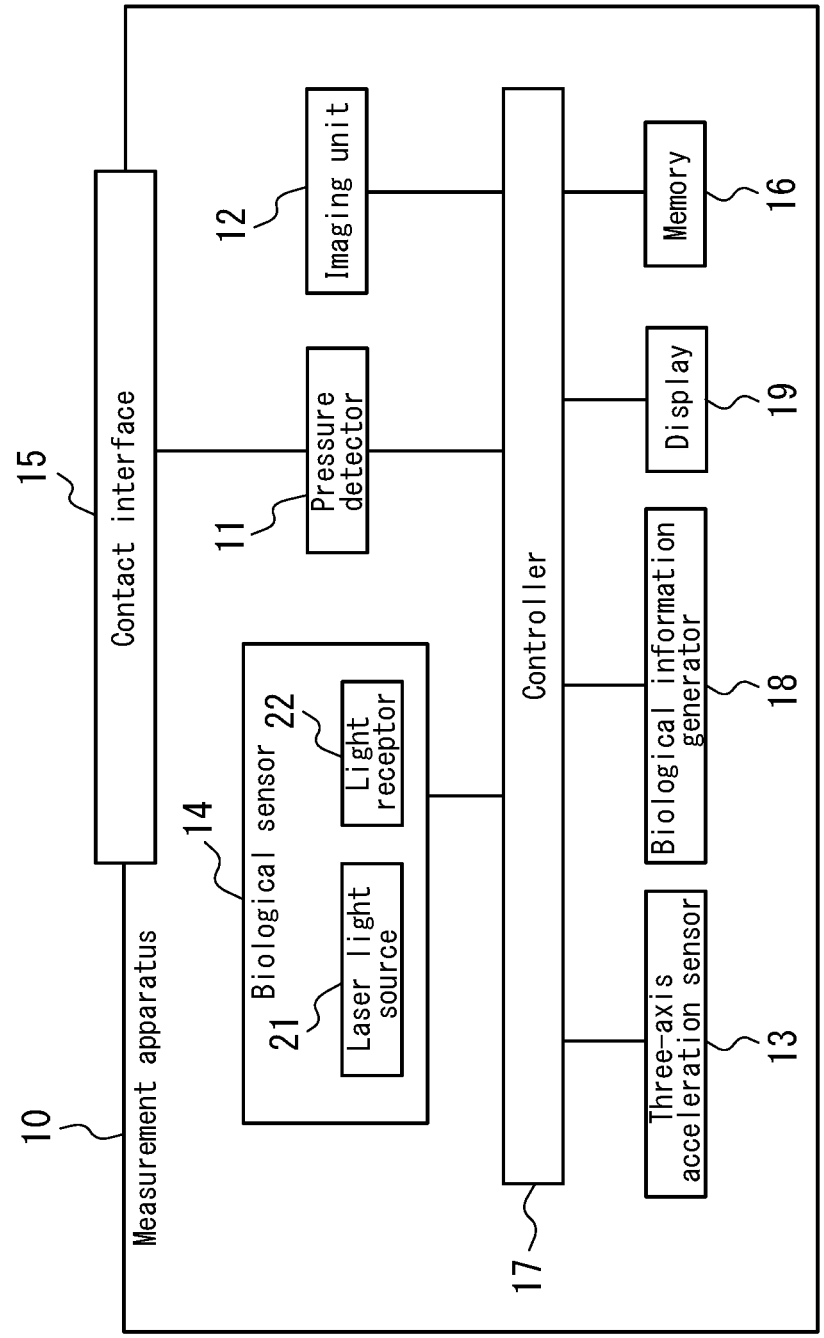
FIG. 3 is a functional block diagram schematically illustrating the structure of the measurement apparatus in FIG. 1.

FIG. 3 is a functional block diagram schematically illustrating the structure of the measurement apparatus 10 in FIG. 1. As illustrated in FIG. 3, the measurement apparatus 10 includes a pressure detector 11, the imaging unit 12, a three-axis acceleration sensor 13, a biological sensor 14, the contact interface 15, a memory 16, a controller 17, a biological information generator 18, and the display 19.

In FIG. 3, the pressure detector 11 detects contact pressure, by the test site, acting on the contact interface 15. The pressure detector 11 may, for example, be configured by a piezoelectric element. The pressure detector 11 is connected to the controller 17 and transmits the detected pressure to the controller 17 as a pressure signal. Accordingly, when the test site is in contact with the contact interface 15, the pressure detector 11 detects the pressure, from the test site, acting on the contact interface 15 and transmits the detected pressure to the controller 17 as a pressure signal.

The imaging unit 12 captures an image at the front face 30a of the measurement apparatus 10, as described above. The imaging unit 12 for example captures live images as a video. The imaging unit 12 transmits information on the captured images to the controller 17. The imaging unit 12 may, for example, launch upon the user performing an operation to launch the imaging unit 12, or the imaging unit 12 may launch together with the biological sensor 14 when the user performs an operation to launch the biological sensor 14.

The three-axis acceleration sensor 13 detects the direction of gravitational force and detects the inclination of the measurement apparatus 10 with reference to the direction of gravitational force. The three-axis acceleration sensor 13 may be configured by a known three-axis acceleration sensor, such as a piezoresistor type, a capacitance type, thermal detection type, or other type of sensor. The three-axis acceleration sensor 13 transmits information on the detected inclination of the measurement apparatus 10 to the controller 17.

The biological sensor 14 acquires biological measurement output from the test site. When the measurement apparatus 10 measures the amount of blood flow, as in this embodiment, then the biological sensor 14 includes a laser light source 21 and a light receiver 22.

The laser light source 21 emits laser light based on control by the controller 17. The laser light source 21 may, for example, be configured to irradiate a test site with laser light, as measurement light, that has a wavelength capable of detecting a predetermined component included in blood. An example of such a laser light source is a Laser Diode (LD).

The light receiver 22 receives scattered measurement light from the test site as biological measurement output. The light receiver 22 may, for example, be configured using a photodiode (PD). The biological sensor 14 transmits a photoelectric conversion signal of the scattered light received by the light receiver 22 to the controller 17.

As described above, the contact interface 15 is a portion that contacts the test site, such as a finger, in order for the user to measure biological information. The contact interface 15 may, for example, be configured by a plate-shaped member. The contact interface 15 may also be configured by a member that is transparent at least with respect to the measurement light and the scattered light from the test site that is in contact.

The memory 16 may be configured with a semiconductor memory or the like. The memory 16 stores a variety of information, programs for causing the measurement apparatus 10 to operate, and the like and also functions as a working memory. The memory 16 may, for example, store the amount of blood flow measured by the measurement apparatus 10 as history.

The memory 16 may store information on a facial image of the user that uses the measurement apparatus 10 to measure the amount of blood flow. In this case, the user takes a picture of his or her own face in advance with the imaging unit 12 and stores (saves) the captured image in the memory 16.

The controller 17 is a processor that, starting with the functional blocks of the measurement apparatus 10, controls and manages the measurement apparatus 10 overall. The controller 17 is configured using a processor such as a Central Processing Unit (CPU) that executes a program prescribing control procedures. Such a program may, for example, be stored in the memory 16, in an external storage medium, or the like.

The controller 17 acquires the output of the light receiver 22 when the pressure on the contact interface 15 as detected by the pressure detector 11 is within a predetermined pressure range. The predetermined pressure range can be any pressure range over which the pressure acting on the contact interface 15 from the test site allows measurement of the amount of blood flow. In particular, a pressure range suitable for measurement of the amount of blood flow by the pressure acting on the contact interface 15 from the test site may be selected. The pressure range suitable for measurement of the amount of blood flow may, for example, be a pressure range such that, based on the statistical relationship between pressure and measurement error, the error in the measurement result of the amount of blood flow falls within a predetermined error range.

When causing laser light to be emitted from the laser light source 21 of the biological sensor 14, the controller 17 causes the display 19 to display an image. The image that the controller 17 causes the display 19 to display may be any image, such as an image that attracts the user's attention. Causing the display 19 to display an image while the controller 17 is causing laser light to be emitted makes it easy for the user to focus on the displayed image. Therefore, it becomes easier for the user to face the front face 30a of the measurement apparatus 10 while the user is measuring biological information. Upon the user facing the front face 30a of the measurement apparatus 10, the laser light that is emitted from the laser light source 21 via the contact interface 15 disposed on the side face 30b is emitted towards the side face 30b, which is to the right when looking at the user's face from the measurement apparatus 10. Therefore, laser light is not emitted towards the user even if the user releases, from the contact interface 15, the thumb that is holding down the contact interface 15. Hence, the chance of laser light entering the user's eye can be reduced. In this way, the measurement apparatus 10 is safer.

When causing laser light to be emitted from the laser light source 21 of the biological sensor 14, the controller 17 for example causes the display 19 to display an image indicating that the amount of blood flow is being measured. The controller 17 may, for example, cause the display 19 to display an image indicating the time until measurement of the amount of blood flow is complete. In greater detail, when measurement of the amount of blood flow ends in five seconds, the controller 17 may cause the display 19 to display an animated image that counts down the five seconds until measurement of the amount of blood flow ends. The controller 17 may also cause the display 19 to display an animated image that counts up for five seconds.

When causing laser light to be emitted from the laser light source 21 of the biological sensor 14, the controller 17 may, for example, cause the display 19 to display an image indicating the state of the blood flow. The image indicating the state of the blood flow may, for example, be an image stored in advance in the memory 16 or may be an image that changes based on the user's amount of blood flow being measured. The image indicating the state of the blood flow may, for example, be an image indicating a slow state of blood flow when the user's amount of blood flow is small and an image indicating a fast state of blood flow when the user's amount of blood flow is large.

The controller 17 may, for example, cause the display 19 to display an image indicating information related to whether the contact pressure on the contact interface 15 as detected by the pressure detector 11 is included in the predetermined pressure range. Information related to whether the pressure on the contact interface 15 is stronger or weaker than the predetermined pressure range may, for example, be included in this image. By displaying such an image, the measurement apparatus 10 can not only make it easier for the user to focus on the display 19, but can also cause the user to recognize information related to pressure, thereby making it easier for the user to achieve an appropriate holding state (contact state of the thumb).

The controller 17 judges whether the acquisition of the biological measurement output by the biological sensor 14 is complete. The controller 17 may, for example, judge that acquisition of the biological measurement output is complete once a predetermined length of time elapses after the biological sensor 14 starts to acquire the biological measurement output. The controller 17 may also, for example, judge that acquisition of the biological measurement output is complete once the biological sensor 14 has acquired sufficient biological measurement output to measure the biological information.

When the user uses the measurement apparatus 10 to measure biological information, the controller 17 controls laser light emitted from the laser light source 21. The controller 17 performs emission control of laser light based on the image captured by the imaging unit 12 or the inclination of the measurement apparatus 10 as detected by the three-axis acceleration sensor 13. Details on emission control of laser light by the controller 17 are provided below.

Based on output of the light receiver 22 (biological information output), the biological information generator 18 generates biological information. The biological information generator 18 may be configured in the measurement apparatus 10 as an independent functional unit that differs from the controller 17, as illustrated in FIG. 3, or may be configured as a portion of the controller 17.

Here, a technique for measurement by the biological information generator 18 of the amount of blood flow using the Doppler shift is now described. When measuring the amount of blood flow, the controller 17 causes laser light to be irradiated from the laser light source 21 onto body tissue (the test site) and receives scattered light that is scattered from the body tissue with the light receiver 22. The biological information generator 18 then calculates the amount of blood flow based on output related to the scattered light that was received.

In the body tissue, scattered light that is scattered from moving blood cells undergoes a frequency shift (Doppler shift), due to the Doppler effect, relative to the speed of travel of the blood cells within the blood. The biological information generator 18 detects the beat signal due to interference between scattered light from still tissue and the scattered light from moving blood cells. This beat signal represents strength as a function of time. The biological information generator 18 then turns the beat signal into a power spectrum that represents power as a function of frequency. In this power spectrum of the beat signal, the Doppler shift frequency is proportional to the speed of blood cells, and the power corresponds to the amount of blood cells. The biological information generator 18 calculates the amount of blood flow by multiplying the power spectrum of the beat signal by the frequency and integrating.

The display 19 is a display device configured by a well-known display such as a liquid crystal display, an organic EL display, an inorganic EL display, or the like. The display 19 for example displays biological information generated by the biological information generator 18.

Next, emission control of laser light by the controller 17 is described in detail. The controller 17 for example controls laser light emitted from the laser light source 21 based on an image captured by the imaging unit 12. In this case, the controller 17 first performs image analysis on the image captured by the imaging unit 12. The controller 17 then refers to the user's facial image stored in the memory 16 to judge whether the user's face is included in the image captured by the imaging unit 12. When judging that the user's face is included in the image captured by the imaging unit 12, the controller 17 permits emission of laser light from the laser light source 21 and causes laser light to be emitted from the laser light source 21. Conversely, when judging that the user's face is not included in the image captured by the imaging unit 12, the controller 17 prohibits emission of laser light from the laser light source 21. When the controller 17 has prohibited emission of laser light, the controller 17 suspends emission of laser light if laser light is being emitted from the laser light source 21.

In this way, the controller 17 permits emission of laser light from the laser light source 21 when the user's face is included in the image captured by the imaging unit 12 and prohibits emission of laser light from the laser light source 21 when the user's face is not included in the image captured by the imaging unit 12. When the user's face is included in the image captured by the imaging unit 12, the user's face is positioned on the front face 30*a* side of the measurement apparatus 10. Therefore, laser light emitted from the laser light source 21 is not emitted towards the user. Accordingly, the chance of laser light entering the user's eye can be reduced, making the measurement apparatus 10 safer.

The controller 17 for example also controls laser light emitted from the laser light source 21 based on the inclination of the measurement apparatus 10 as detected by the three-axis acceleration sensor 13. In greater detail, the controller 17 judges the emission direction of laser light emitted from the laser light source 21 based on the inclination of the measurement apparatus 10 as detected by the three-axis acceleration sensor 13. When judging that the emission direction of laser light is a predetermined angle or greater relative to the vertically upward direction, the controller 17 permits emission of laser light from the laser light source 21 and causes laser light to be emitted from the laser light source 21. When judging that the emission direction of laser light is less than a predetermined angle relative to the vertically upward direction, the controller 17 prohibits emission of laser light from the laser light source 21. When the controller 17 has prohibited emission of laser light, the controller 17 suspends emission of laser light if laser light is being emitted from the laser light source 21.

In this way, the controller 17 permits emission of laser light from the laser light source 21 when the emission direction of laser light is a predetermined angle or greater relative to the vertically upward direction and prohibits emission of laser light from the laser light source 21 when the emission direction is less than a predetermined angle relative to the vertically upward direction. When measuring the amount of blood flow with the measurement apparatus 10, it is assumed that normally the user's upper body is upright, and the user measures the amount of blood flow by holding the measurement apparatus 10 at a lower position than the face, such as in front of the chest. When the user and the measurement apparatus 10 are in such a positional relationship and the emission direction of the laser light is a predetermined angle or greater relative to the vertically upward direction, then the laser light is not emitted towards the user, who is positioned upward from the measurement apparatus 10. Accordingly, the chance of laser light entering the user's eye can be reduced, making the measurement apparatus 10 safer. The predetermined angle may be set taking into account the holding state of the measurement apparatus 10 by the user and may, for example, be 45°.

The measurement apparatus 10 according to this embodiment includes both the imaging unit 12 and the three-axis acceleration sensor 13. Therefore, the controller 17 can perform emission control of laser light based on an appropriate selection of the image captured by the imaging unit 12 or the inclination of the measurement apparatus 10 as detected by the three-axis acceleration sensor 13, or based on both. When the location where the image is captured is dark, for example, making it impossible for image analysis to judge whether the user's face is included in the image, then the controller 17 performs emission control of laser light based on the inclination of the measurement apparatus 10 as detected by the three-axis acceleration sensor 13. When, for example, performing emission control of laser light based on both approaches, the controller 17 can judge that the user's face is not included in the captured image and can prohibit emission of laser light when the emission direction of laser light is a predetermined angle or greater relative to the vertically upward direction, but the user is looking into the emission hole for laser light from the horizontal direction.

Next, an example of how the controller 17 performs emission control of laser light with respect to the laser light source 21 is described with reference to the flowchart in FIG. 4. The processing of the flowchart in FIG. 4 for example begins when the measurement apparatus 10 enters a state capable of measuring the amount of blood flow as a result of an operation on the measurement apparatus 10. At the start of this process, laser light is not being emitted from the laser light source 21. In the flowchart in FIG. 4, as one example the controller 17 is described as performing emission control of laser light based on both the image captured by the imaging unit 12 and the inclination of the measurement apparatus 10 as detected by the three-axis acceleration sensor 13.

The controller 17 displays information related to pressure on the contact interface 15 on the display 19 (step S101). This information is, for example, information related to whether the pressure on the contact interface 15 is stronger or weaker than the predetermined pressure range.

Next, the controller 17 judges whether the pressure acting on the contact interface 15 as detected by the pressure detector 11 is within a predetermined pressure range (step S102).

When judging that the pressure acting on the contact interface 15 is not within the predetermined pressure range (step S102: No), the controller 17 prohibits emission of laser light. Hence, laser light is not emitted. The controller 17 repeats step S102 until judging that pressure acting on the contact interface 15 is within the predetermined pressure range.

When judging that the pressure acting on the contact interface 15 is within the predetermined pressure range (step S102: Yes), the controller 17 then judges whether the user's face is included in the image captured by the imaging unit 12 (step S103).

When judging that the user's face is not included in the image captured by the imaging unit 12 (step S103: No), the controller 17 prohibits emission of laser light. Hence, laser light is not emitted. Processing then returns to step S102.

When judging that the user's face is included in the image captured by the imaging unit 12 (step S103: Yes), the controller 17 then judges whether the emission direction of laser light is a predetermined angle or greater relative to the vertically upward direction, based on the inclination of the measurement apparatus 10 as detected by the three-axis acceleration sensor 13 (step S104).

When judging that the emission direction of laser light is less than a predetermined angle (step S104: No), the controller 17 prohibits emission of laser light. Hence, laser light is not emitted, and processing returns to step S102.

When judging that the emission direction of laser light is a predetermined angle or greater (step S104: Yes), the controller 17 permits emission of laser light and emits laser light from the laser light source 21. By emission of laser light, the light receiver 22 receives scattered light, and acquisition of biological measurement output begins in the biological sensor 14 (step S105).

Next, as in step S102, the controller 17 judges whether the pressure acting on the contact interface 15 as detected by the pressure detector 11 is within a predetermined pressure range (step S106).

When judging that the pressure acting on the contact interface 15 is not within the predetermined pressure range (step S106: No), the controller 17 prohibits emission of laser light. Hence, emission of laser light from the laser light source 21 is suspended (step S109). Processing then returns to step S102.

Conversely, when judging that the pressure acting on the contact interface 15 is within the predetermined pressure range (step S106: Yes), then as in step S103, the controller 17 judges whether the user's face is included in the image captured by the imaging unit 12 (step S107).

When judging that the user's face is not included in the image captured by the imaging unit 12 (step S107: No), the controller 17 prohibits emission of laser light. Hence, emission of laser light from the laser light source 21 is suspended (step S109). Processing then returns to step S102.

When judging that the user's face is included in the image captured by the imaging unit 12 (step S107: Yes), then as in step S104, the controller 17 judges whether the emission direction of laser light is a predetermined angle or greater relative to the vertically upward direction (step S108).

When judging that the emission direction of laser light is less than a predetermined angle (step S108: No), the controller 17 prohibits emission of laser light. Hence, emission of laser light from the laser light source 21 is suspended (step S109). Processing then returns to step S102.

Conversely, when judging that the emission direction of laser light is a predetermined angle or greater (step S108: Yes), the controller 17 judges whether acquisition of the biological measurement output by the biological sensor 14 has finished while maintaining the state of emission of laser light from the laser light source 21 (step S110).

When judging that acquisition of biological measurement output is not finished (step S110: No), the controller 17 returns to step S106 and judges whether the pressure acting on the contact interface 15 is within a predetermined pressure range.

When judging that acquisition of biological measurement output is finished (step S110: Yes), the controller 17 suspends emission of laser light from the laser light source 21 (step S111). Acquisition of biological measurement output in the measurement apparatus 10 is completed in this way. The acquired biological measurement output is used by the biological information generator 18 to generate biological information.

In this way, the measurement apparatus 10 according to this embodiment includes the contact interface 15, through which laser light from the laser light source 21 is emitted, on the side face 30b that differs from the front face 30a. Therefore, when the user measures the amount of blood flow using the measurement apparatus 10, the laser light emitted from the side face 30b is not easily emitted towards the face of the user, who is performing an operation while looking at the front face 30a. Based on the guide 40, the user can contact the test site to the contact interface 15 while orienting the front face 30a towards the user. Accordingly, the measurement apparatus 10 is safer.

This disclosure is not limited to the above embodiments, and a variety of modifications and changes are possible. For example, the functions and the like included in the various components and steps may be reordered in any logically consistent way. Furthermore, components or steps may be combined into one or divided.

For example, the position of the contact interface 15 is not limited to the position illustrated in FIG. 1. The contact interface 15 may be disposed at any position that is on a different surface than the front face 30a of the measurement apparatus 10 and is such that the user can cover the contact interface 15 with the pad of a finger without a sense of awkwardness when holding the measurement apparatus 10. For example, the contact interface 15 may be disposed at a different position on the side face 30b of the measurement apparatus 10, on a different side from the side face 30b, or on the back. The user may measure biological information by contacting a different finger than the thumb to the contact interface 15.

The measurement apparatus 10 is not limited to one contact interface 15. The measurement apparatus 10 may include two or more contact interfaces. For example, in addition to the position illustrated for the contact interface 15 in FIG. 1, the measurement apparatus 10 may include another contact interface on the side opposite the contact interface 15 in FIG. 1, at a position that is symmetrical with the contact interface 15 when looking at the front face 30a of the measurement apparatus 10. The measurement apparatus 10 includes a guide that indicates the positions of each of the contact interfaces. The contact interfaces are each connected to a pressure detector. In this case, the user can contact the contact interface with either the right or left thumb by holding the measurement apparatus 10 with either the right or left hand. When the measurement apparatus 10 includes a plurality of contact interfaces, the controller 17 for example emits laser light in the direction of the contact interface corresponding to the pressure detector that detected pressure. As a result, the controller 17 can prevent laser light from being emitted from a contact interface 15 that is not being contacted by a finger.

In the above embodiment, the controller 17 is described as performing emission control of laser light based on whether the emission direction of laser light is a predetermined angle or greater with reference to the vertically upward direction, but the reference for the predetermined angle need not be the vertically upward direction. For example, when users measure biological information using the measurement apparatus 10 while lying on their back, the controller 17 may perform emission control of laser light based on whether or not the emission direction of laser light is a predetermined angle or greater with reference to the vertically downward direction.

The invention claimed is:

1. A measurement apparatus comprising:
   a housing;
   a display disposed on a front face of the housing;
   an imaging device disposed on the front face of the housing;
   a contact interface, to be contacted by a test site, disposed on a different surface than the front face of the housing;
   a laser light source configured to emit laser light from the contact interface;
   a light receiver configured to receive scattered laser light from the test site; and
   a controller including a processor configured to:
      generate biological information based on output from the light receiver; and
      control emission of laser light by the laser light source, wherein
   the controller permits emission of the laser light from the laser light source when a face of a subject is included in an image captured by the imaging device and prohibits emission of the laser light from the laser light source when the face of the subject is not included in the image.

2. The measurement apparatus of claim 1, further comprising a guide indicating a position of the contact interface.

3. The measurement apparatus of claim 1, wherein when causing laser light to be emitted from the laser light source, the controller causes the display to display an image.

4. The measurement apparatus of claim 1, further comprising:
   a three-axis acceleration sensor configured to detect an inclination of the housing with reference to a direction of gravitational force, wherein
   the controller judges whether an emission direction of the laser light is a predetermined angle or greater from a vertically upward direction based on the inclination detected by the three-axis acceleration sensor, permits emission of the laser light from the laser light source when the emission direction is the predetermined angle or greater, and prohibits emission of the laser light from the laser light source when the emission direction is less than the predetermined angle.

5. The measurement apparatus of claim 4, wherein the predetermined angle is 45°.

6. The measurement apparatus of claim 1, wherein the biological information includes information related to blood flow.

* * * * *